US010399048B2

(12) United States Patent
Siow et al.

(10) Patent No.: US 10,399,048 B2
(45) Date of Patent: Sep. 3, 2019

(54) SAMPLE PROCESSING APPARATUS WITH INTEGRATED HEATER, SHAKER AND MAGNET

(71) Applicant: Agilent Technologies, Inc., Santa Clara, CA (US)

(72) Inventors: Chai Siong Siow, Penang (MY); Thuan-Khim Khor, Penang (MY); David Knorr, San Leandro, CA (US)

(73) Assignee: Agilent Technologies, Inc., Santa Clara, CA (US)

( * ) Notice: Subject to any disclaimer, the term of this patent is extended or adjusted under 35 U.S.C. 154(b) by 142 days.

(21) Appl. No.: 15/668,039

(22) Filed: Aug. 3, 2017

(65) Prior Publication Data

US 2019/0039034 A1 Feb. 7, 2019

(51) Int. Cl.
 *B01F 11/00* (2006.01)
 *B01L 7/00* (2006.01)
 (Continued)

(52) U.S. Cl.
 CPC ...... *B01F 11/0014* (2013.01); *B01F 11/0031* (2013.01); *B01F 11/0034* (2013.01); *B01L 7/52* (2013.01); *B01L 7/525* (2013.01); *B03C 1/01* (2013.01); *B03C 1/0332* (2013.01); *B03C 1/0335* (2013.01); *B03C 1/28* (2013.01); *B03C 1/288* (2013.01); *B03C 1/30* (2013.01); *G01N 1/28* (2013.01); *B01L 9/06* (2013.01); *B01L 2200/0668* (2013.01); *B03C 2201/18* (2013.01); *B03C 2201/26* (2013.01); *G01N 1/44* (2013.01); *G01N 35/00* (2013.01); *G01N 35/0098* (2013.01)

(58) Field of Classification Search
None
See application file for complete search history.

(56) References Cited

U.S. PATENT DOCUMENTS 5,443,791 A * 8/1995 Cathcart ............. B01L 3/50825
422/561
6,193,892 B1 2/2001 Krueger et al.
(Continued)

FOREIGN PATENT DOCUMENTS

WO 2011047233 A1 4/2011

OTHER PUBLICATIONS

International Search Report and Written Opinion issued in counterpart PCT Application No. PCT/US2018/035530 dated Jan. 21, 2019 (fourteen (14) pages).

*Primary Examiner* — Paul M. West
*Assistant Examiner* — Mark A Shabman

(57) ABSTRACT

Samples in an array of containers are processed by mounting the containers on a sample stage, moving magnets into proximity with bottoms of the containers of a first column of containers to apply a magnetic field, moving the magnets into proximity with bottoms of the containers of a second column, and moving heater elements into proximity with the container bottoms of the first column. While the magnetic field is applied to the containers of the second column, heat energy may be applied to the containers of the first column. The process may be repeated for additional columns. The containers may also be shaken to agitate the samples. A single apparatus may perform heating, shaking, and magnetic field application, without needing to transport the containers to different stations.

20 Claims, 11 Drawing Sheets

(51) Int. Cl.
  *B03C 1/30* (2006.01)
  *B03C 1/28* (2006.01)
  *G01N 1/28* (2006.01)
  *B03C 1/01* (2006.01)
  *B03C 1/033* (2006.01)
  *B01L 9/06* (2006.01)
  *G01N 35/00* (2006.01)
  *G01N 1/44* (2006.01)

(56) References Cited

U.S. PATENT DOCUMENTS

| | | | |
|---|---|---|---|
| 6,368,561 B1 | 4/2002 | Rutishauser et al. | |
| 6,906,292 B2 | 6/2005 | Weinfield et al. | |
| 7,264,111 B2* | 9/2007 | Veiner | G01N 35/04 198/465.1 |
| 7,338,199 B2 | 3/2008 | Hafner | |
| 7,776,221 B2 | 8/2010 | Brassard | |
| 8,161,831 B2* | 4/2012 | Fukuma | G01N 35/026 73/864.21 |
| 8,393,781 B2* | 3/2013 | Manera | B01F 11/0008 366/112 |
| 8,573,071 B2 | 11/2013 | Krueger et al. | |
| 8,691,149 B2 | 4/2014 | Fritchie et al. | |
| 8,984,968 B2* | 3/2015 | Bonk | B01F 11/0014 73/863.11 |
| 9,134,333 B2* | 9/2015 | Kuwano | G01N 35/02 |
| 9,140,634 B1 | 9/2015 | Knippschild et al. | |
| 9,260,763 B2 | 2/2016 | Thomas et al. | |
| 9,335,338 B2* | 5/2016 | Ochranek | G01N 35/025 |
| 9,618,139 B2 | 4/2017 | Handique | |
| 2007/0110617 A1* | 5/2007 | Nagai | G01N 35/026 422/65 |
| 2009/0040866 A1* | 2/2009 | Rollin, III | B01F 11/0014 366/219 |
| 2010/0173394 A1* | 7/2010 | Colston, Jr. | B01F 3/0807 435/287.2 |
| 2011/0088491 A1* | 4/2011 | Krueger | B01F 11/0014 73/863.11 |
| 2015/0079586 A1 | 3/2015 | Keller et al. | |
| 2017/0128946 A1 | 5/2017 | Williams et al. | |
| 2018/0001285 A1* | 1/2018 | Sung | B01F 11/0014 |

\* cited by examiner

SAMPLE PROCESSING APPARATUS WITH INTEGRATED HEATER, SHAKER AND MAGNET

TECHNICAL FIELD

The present invention generally relates to processing samples, such as biological or chemical samples residing in a liquid, by heating, shaking, and magnetic-based separation. In particular, the invention relates to an apparatus that integrates heating, orbital shaking, and magnetic beads separation.

BACKGROUND

Many methods for processing and analyzing samples involve the steps of heating, shaking, and applying a magnetic field to the samples such as for extracting target compounds from the samples. Conventionally, the three steps of heating, shaking, and applying a magnetic field are performed at three independent and separate stations, for example utilizing a shaker, a magnetic separation device, and a heater.

One example is a class of methods implementing the hybridization and purification of DNA from blood samples. A sample consisting of DNA carried in liquid buffer is provided in the sample container. Magnetic beads are added to the container. The magnetic beads may be functionalized as needed to allow the DNA molecules to bind to the beads. The container is then mounted to a shaker such as an orbital shaker. The shaker agitates the sample to obtain a homogenous mixture of the magnetic beads with the sample, enhancing the yield of DNA bound to the magnetic beads. After shaking, the sample is removed from the shaker and transported to a magnetic separation device. The sample is dispensed into a tube and the tube is mounted to a tube holder of the magnetic separation device. The magnetic separation device includes permanent magnets positioned near the side of the tube. The permanent magnets attract the magnetic beads to the side of the tube, thereby concentrating the magnetic beads at one region in the tube. The buffer is then removed from the tube and replaced with ethanol as a wash step. The sample is then transported back to the shaker, and the shaker is operated again to disperse the ethanol and the magnetic beads in the tube. The sample is then transported back to the magnetic separation device to again concentrate the magnetic beads. The foregoing steps of shaking and magnetic beads separation may be repeated one or more times. The sample is then removed from the magnetic separation device and transported to a heater block. Heating by the heater block evaporates the ethanol, and the magnetic beads are allowed to air-dry. The DNA may then be eluted from the magnetics beads by a suitable solvent wash step.

The conventional process of heating, shaking, and applying a magnetic field is disadvantageous. The presence of the three separate stations required for heating, shaking, and magnetic-based separation consumes excessive space on a workbench. The use of three separate stations requires samples to be manually handled and transported from one station to another station, which is time consuming and creates the potential for contamination of the samples. Accordingly, there is a need to address these problems.

SUMMARY

To address the foregoing needs, in whole or in part, and/or other needs that may have been observed by persons skilled in the art, the present disclosure provides methods, processes, systems, apparatus, instruments, and/or devices, as described by way of example in implementations set forth below.

According to one embodiment, a sample processing apparatus includes: a sample stage having an opening and configured to support a sample support such that the sample support covers the opening; a first stage configured to move along a first axis; a second stage configured to move alternately toward and away from the opening along a second axis orthogonal to the first axis, the second stage coupled to the first stage wherein the second stage is movable with the first stage along the first axis; a plurality of heater elements disposed on the second stage and linearly positioned along a third axis orthogonal to the first axis and the second axis; and a plurality of magnets disposed on the second stage and linearly positioned along the third axis, wherein: the magnets are positioned adjacent to the heater elements such that each magnet is spaced from a respective one of the heater elements along the first axis; the first stage is configured to sequentially move the heater elements and the magnets to a plurality of column positions along the first axis, wherein at each column position, at least the heater elements or the magnets are aligned with a column of sample containers of the sample support when the sample support is mounted to the sample stage, the column being arranged along the third axis; and the second stage is configured to, at each column position, move the heater elements and the magnets between an upper position at which the heater elements and the magnets are proximate to the sample support when the sample support is mounted to the sample stage, and lower position at which the heater elements and the magnets are remote from the sample support.

In an embodiment, the sample processing apparatus includes a controller configured to control movements of the first stage and the second stage.

According to another embodiment, a method for processing a sample includes: providing a sample support comprising a plurality of sample containers arranged as an array of a plurality of columns and a plurality of rows, wherein the plurality of columns comprises at least a first column and a second column adjacent to the first column, the first column contains one or more samples in one or more respective sample containers of the first column, and the second column contains one or more samples in one or more respective sample containers of the second column; mounting the sample support to a sample stage such that the sample support covers an opening of the sample stage, wherein the opening has an area allowing the sample containers to be exposed through the opening; moving a plurality of magnets into proximity with bottoms of the sample containers of the first column; applying magnetic fields generated by the magnets to the sample containers of the first column to expose the one or more samples of the first column to one or more of the magnetic fields; moving the plurality of magnets into proximity with bottoms of the sample containers of the second column, while the sample support remains mounted to the sample stage; moving a plurality of heater elements into proximity with the bottoms of the sample containers of the first column; and applying heat energy emitting from the heater elements to the sample containers of the first column to expose the one or more samples of the first column to the heat energy.

In an embodiment, the sample containers are spaced from each other by a container-to-container pitch, the heater elements are spaced from each other by a heater-to-heater pitch equal to the container-to-container pitch, the magnets are spaced from each other by a magnet-to-magnet pitch equal to the container-to-container pitch, and each magnet is spaced from a respective one of the heater elements by a magnet-to-heater pitch equal to the container-to-container pitch.

Other devices, apparatus, systems, methods, features and advantages of the invention will be or will become apparent to one with skill in the art upon examination of the following figures and detailed description. It is intended that all such additional systems, methods, features and advantages be included within this description, be within the scope of the invention, and be protected by the accompanying claims.

BRIEF DESCRIPTION OF THE DRAWINGS

The invention can be better understood by referring to the following figures. The components in the figures are not necessarily to scale, emphasis instead being placed upon illustrating the principles of the invention. In the figures, like reference numerals designate corresponding parts throughout the different views.

DETAILED DESCRIPTION

As used herein, the term "fluid" is used in a general sense to refer to any substance that is flowable through a conduit. Thus, the term "fluid" may generally refer to either a liquid or a gas, unless specified otherwise or the context dictates otherwise.

As used herein, the term "liquid" generally refers to a flowable substance. A liquid may be part of a mixture that also includes a material such as, for example, (bio)chemical compounds, beads, or other particles. In such case, the liquid may be characterized as including or containing the material, or the material may be characterized as being in, or carried in or by, the liquid. The material may be "carried" in the liquid by any mechanism. As examples, the liquid-material mixture may be a solution, a suspension, a colloid, or an emulsion. Solid particles and/or gas bubbles may be present in the liquid.

As used herein, the term "(bio)chemical compound" encompasses chemical compounds and biological compounds. A chemical compound may, for example, be a small molecule or a high molecular-weight molecule (e.g., a polymer). A biological compound may be, for example, a biopolymer.

The terms "nucleic acid" and "polynucleotide" are used interchangeably herein to describe a polymer of any length, e.g., greater than about 2 bases, greater than about 10 bases, greater than about 100 bases, greater than about 500 bases, greater than 1000 bases, or up to about 10,000 or more bases composed of nucleotides, e.g., deoxyribonucleotides or ribonucleotides, and may be produced enzymatically or synthetically (e.g., PNA as described in U.S. Pat. No. 5,948,902 and the references cited therein) and which can hybridize with naturally occurring nucleic acids in a sequence specific manner analogous to that of two naturally occurring nucleic acids, e.g., can participate in Watson-Crick base pairing interactions. In addition to deoxyribonucleic acid (DNA) and ribonucleic acid (RNA), the terms "nucleic acid" and "polynucleotide" may encompass peptide nucleic acid (PNA), locked nucleic acid (LNA), and unstructured nucleic acid (UNA).

Figure 1:
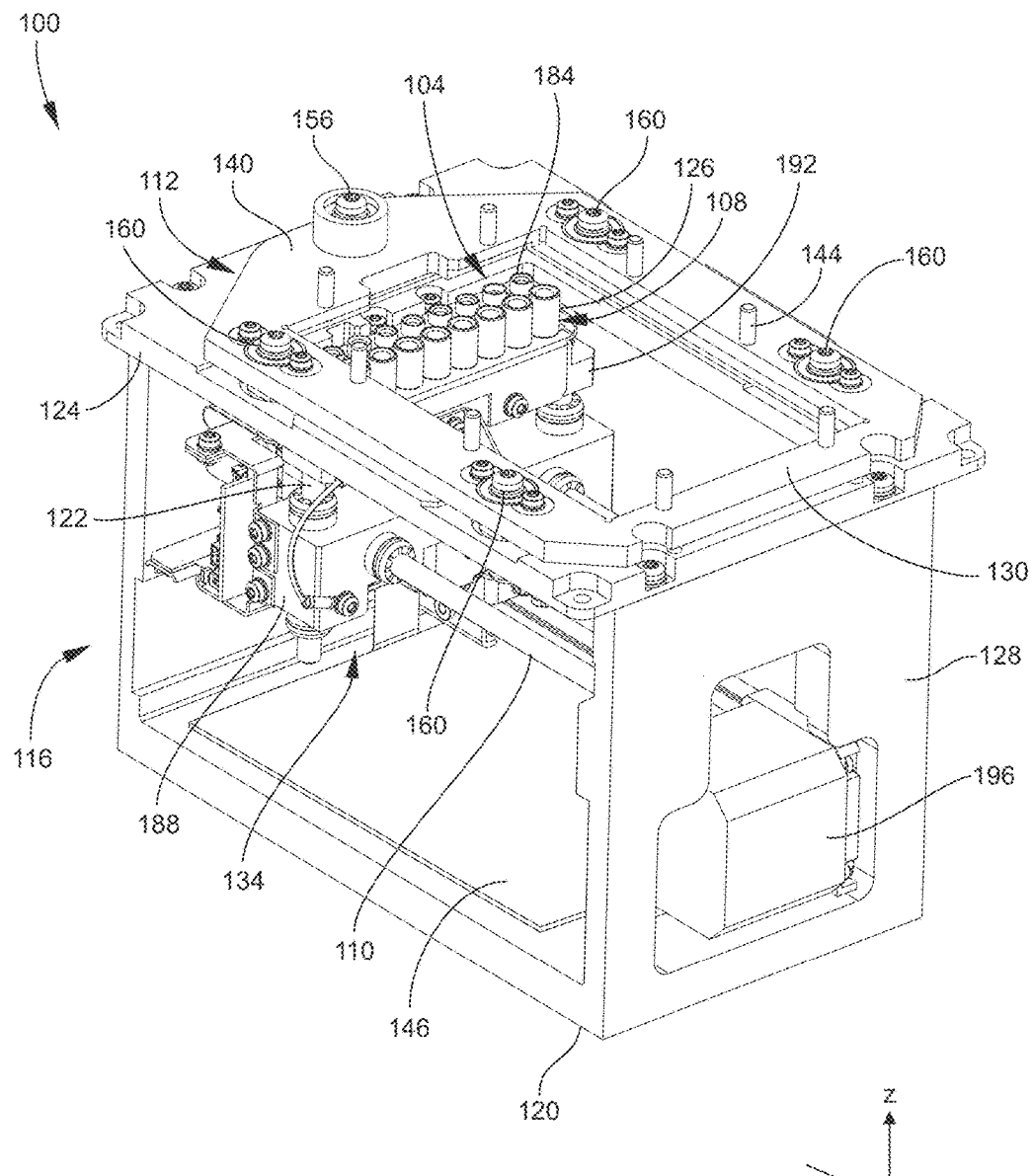
FIG. 1 is a perspective view of an example of a sample processing apparatus according to an embodiment.
Figure 2:
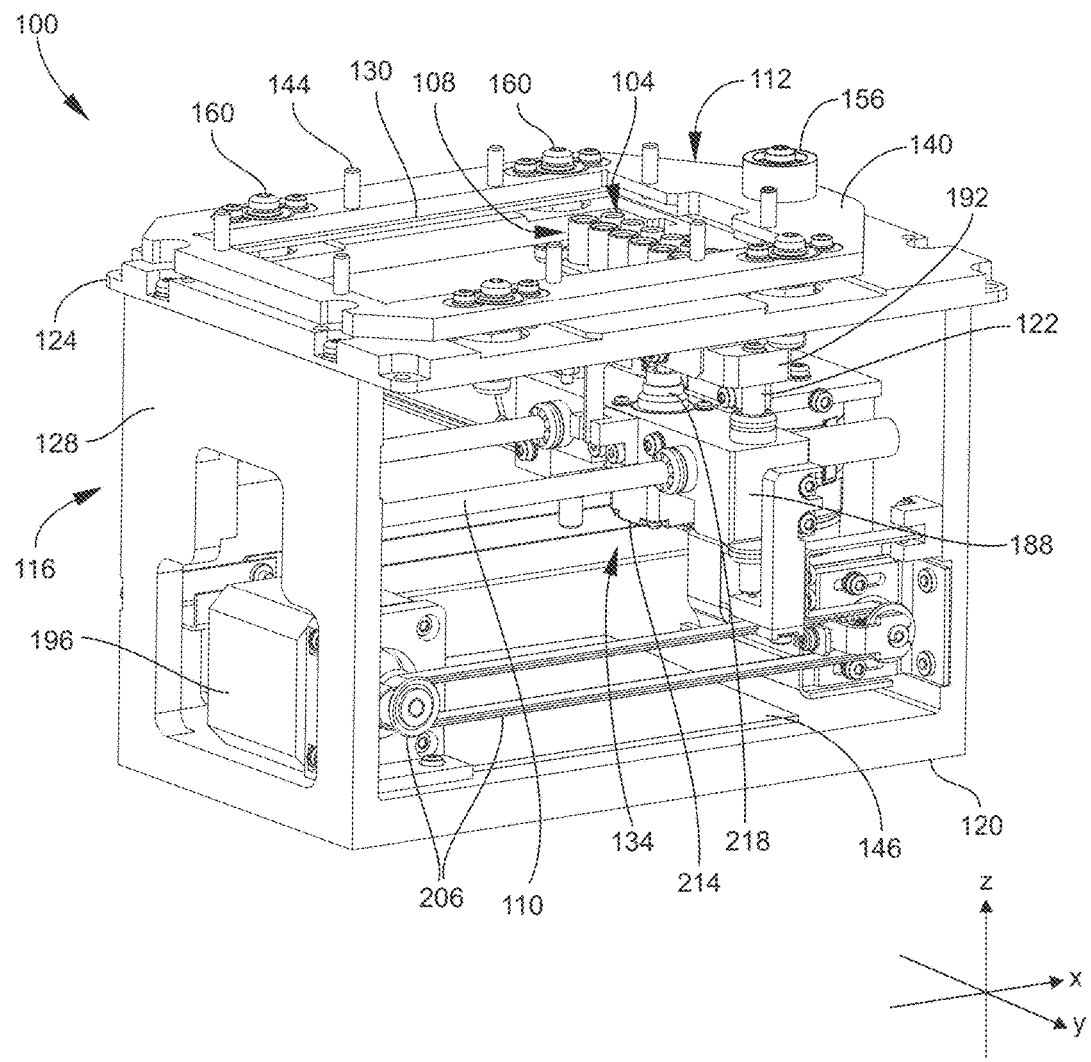
FIG. 2 is another perspective view of the sample processing apparatus, from a side opposite to that shown in FIG. 1.

FIG. 1 is a perspective view of an example of a sample processing apparatus 100 according to an embodiment. FIG. 2 is another perspective view of the sample processing apparatus 100 from a side opposite to that shown in FIG. 1. For descriptive purposes, FIGS. 1 and 2 (and other drawing figures) include a Cartesian coordinate (X, Y, Z) frame of reference, the origin of which has been arbitrarily located relative to the illustrated apparatus 100. Typically, the X-axis and Y-axis lie in a horizontal plane such that the Z-axis is oriented in a vertical direction. These axes are alternatively referred to as directions. For descriptive purposes, the X-axis, Z-axis, and Y-axis are alternatively referred to as the first axis or direction, the second axis or direction, and the third axis or direction, respectively.

The apparatus 100 is configured to perform heating, shaking (agitating), and magnetic beads separation (separation of analytes using magnetic beads) of samples as described further below. To implement these functions, the apparatus 100 generally includes a heater 104, a magnet assembly 108, and a shaker 112. The apparatus 100 also generally includes a frame 116 supporting the heater 104, magnet assembly 108, shaker 112, and various other components of the apparatus 100. The frame 116 may include one or more structures such as a lower plate or base 120, an upper plate 124, and one or more lateral walls (or beams) 128 extending (typically vertically) between the base 120 and the upper plate 124.

The apparatus 100 may be a stand-alone apparatus that integrates the operations of heating, shaking, and magnetic beads separation. The apparatus 100 may be enclosed in a housing (not shown). The housing (if provided) may be configured to isolate the apparatus 100, including samples being processed by the apparatus 100, from the ambient. The housing may be configured to provide a substantially dust-free environment. The housing may be configured to provide environmental control, for example in terms of temperature, pressure, humidity, etc. The apparatus 100 may be part of (e.g., inside of, connected to, or proximate to) an associated system. Thus, the base 120 may be disposed on a suitable surface such as a bench or table, or on a surface of a housing or an associated system that itself is disposed on a suitable surface such as a bench or table. The associated system (if provided) may be any apparatus or system configured to perform functions relating to sample preparation, processing, and/or analysis. As examples, the associated system may be configured for labware handling (e.g., robotic gripping and transport), liquid handling (e.g., aspiration, transport, and dispensing of samples, solutions, solvents, reagents, labels such as dyes, etc., such as with a pipettor and associated pumps, valves, and tubing), sample preparation (e.g., addition of liquids such as reagents, buffers, diluents, etc.), sample detection or measurement (e.g., optics-based detection/measurement or imaging such as based on fluorescence, luminescence, absorbance, microscopy, etc.), optical reading of barcodes or other indicia uniquely identifying samples or sample containers, etc.

The apparatus 100 may be configured to process one or more samples, and may be configured to process a plurality of samples simultaneously. One or more of the samples (and/or the liquid in which they reside) may be different from each other, or all samples may be the same. One or more samples may be supported in one or more respective sample containers. The shaker 112 is configured to receive one or more sample containers in a manner effective to transfer the shaking action generated by the shaker 112 to the container(s), and to keep the container(s) secured to the shaker 112 during shaking. Thus, the shaker 112 is configured such that the container(s) mounted thereto will move in accordance with the shaking action. In some embodiments, the shaker 112 is additionally configured such that the container(s) mounted thereto will move with the shaking (moving) component of the shaker 112, but will not move relative to the shaking component.

Figure 3:
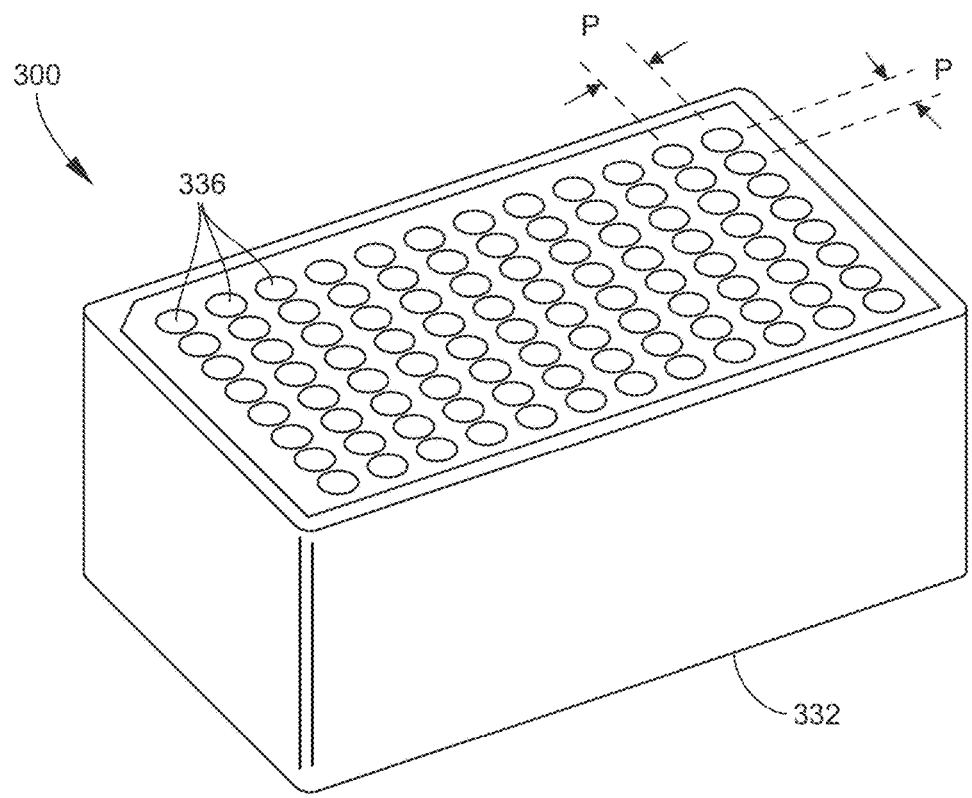
FIG. 3 is a perspective view of an example of sample support that may be utilized with the sample processing apparatus illustrated in FIG. 1 according to an embodiment.
Figure 3:
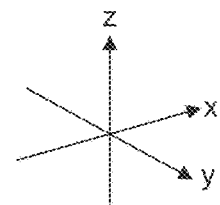

FIG. 3 is a perspective view of an example of sample support 300 that may be utilized with the apparatus 100 according to an embodiment. In this embodiment, the sample support 300 includes a support structure 332 configured to define or support a plurality of individual sample containers 336 (chambers, wells, etc.) in which individual samples may be respectively contained. In the illustrated embodiment, the sample support 300 is a multi-well microtiter plate, or microplate, which includes a two-dimensional array of wells (sample containers 336). In a typical embodiment, the two-dimensional array is a 2:3 rectangular matrix of wells. In the present embodiment, the sample support 300 includes twelve columns and eight rows of wells, for a total number of 96 wells. In the illustrated example, the sample containers 336 in each column are linearly positioned and spaced from each other along the Y-axis (third axis or direction), the columns are adjacent to each other along the X-axis (first axis or direction), the sample containers 336 in each row are linearly positioned and spaced from each other along the X-axis, and the rows are adjacent to each other along the Y-axis. The configuration of the array of wells may be in accordance with a standard format such as the American National Standards Institute/Society for Laboratory Automation and Screening (ANSI/SLAS) standards for multi-well plates current at the time of filing the present disclosure. The pitch of the wells (or other type of sample containers 336), e.g. the distance between the centers of two adjacent wells, referred to herein as the well-to-well pitch P, may be uniform throughout the array. For example, the well-to-well pitch P may be as specified by ANSI/SLAS 4-2004 (R2012): Microplates—Well Positions. Hence, in one non-limiting example the well-to-well pitch P is 9.0 mm in the case of a 96-well format, or about 9.0 mm when considering the positional tolerances specified by ANSI/SLAS 4-2004.

In other embodiments, the number of columns may be more or less than twelve and the number of rows may be more or less than eight. The cross-sections of the wells (or other type of sample containers 336) in the X-Y plane may be cylindrical (as illustrated) or polygonal. The side profiles of the wells along their depth (Z-axis) may be straight or tapered, and may have one or more transitions at which cross-sections are appreciably reduced (stepped down). All or part of the sample support 300 (e.g., the bottoms of the sample containers 336) may be optically transparent to enable optical reading. In other embodiments, the sample containers 336 may be removable from the support structure 332. For example, the support structure 332 may be a rack or the like and the sample containers 336 may be vials or the like that are supported by the rack.

Figure 4:
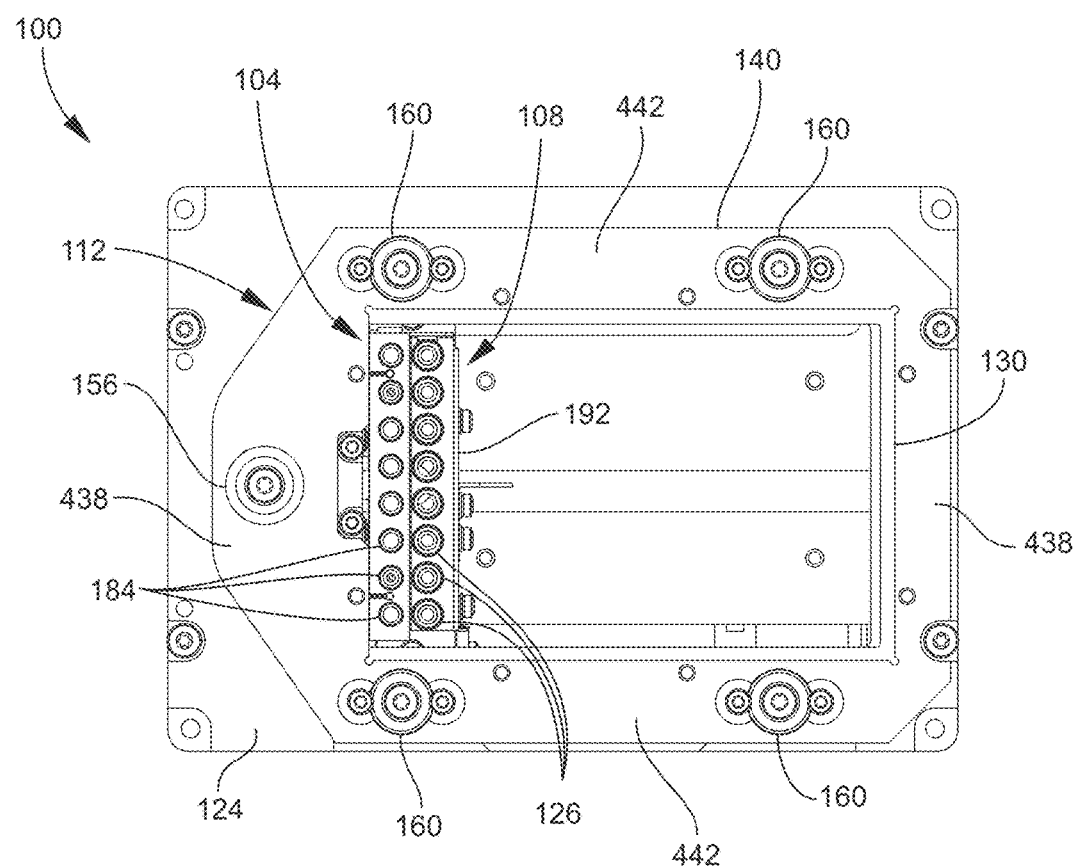
FIG. 4 is a top view of the sample processing apparatus illustrated in FIG. 1.
Figure 5:
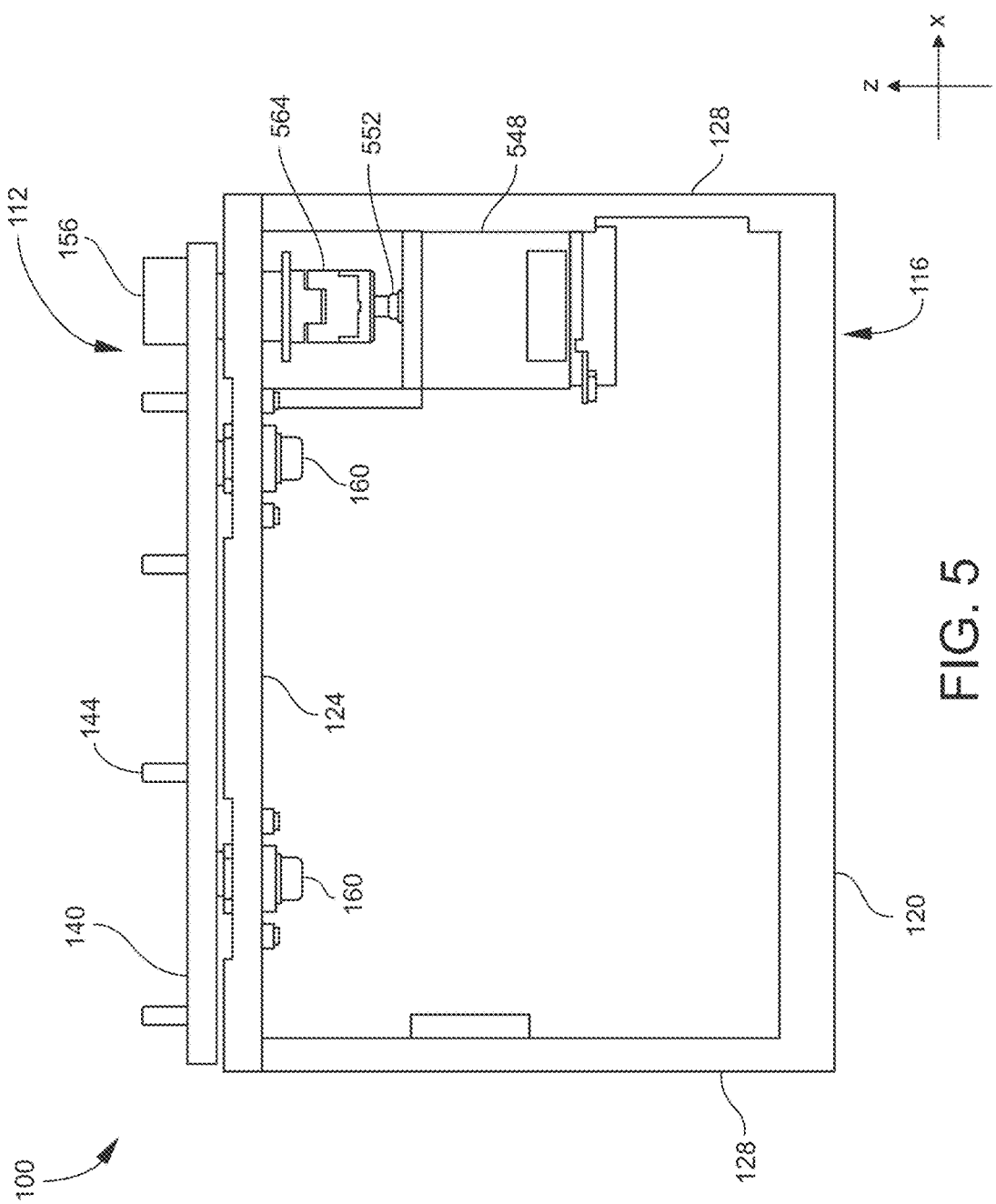
FIG. 5 is a side view of the sample processing apparatus illustrated in FIG. 1, with various components removed to primarily show a shaker and a frame.

FIGS. 1, 2, and 4-7 illustrate components of the shaker 112. FIG. 4 is a top view of the apparatus 100. FIG. 5 is a side view of the apparatus 100, with various components removed to primarily show the shaker 112 and the frame 116. The shaker 112 includes a sample (or shaker) stage (or platform) 140 upon which a sample support (e.g., the sample support 300 illustrated in FIG. 3) is mounted. The sample stage 140 is movable to perform the shaking action. The sample stage 140 may include mounting features 144 of any suitable configuration for coupling to complementary mounting features (not shown) of or engaged with the sample support 300, thereby enabling the sample support 300 to be securely mounted to the sample stage 140. As best shown in FIG. 5, the shaker 112 further includes a motor 548 (e.g., a DC motor such as a brushless DC motor) with an output shaft 552 rotated by the motor 548. The motor 548 drives the motion of the sample stage 140 (thereby shaking the sample support 300 and sample(s) contained by the sample support 300) via the rotating output shaft 552 and a suitable transmission linkage coupled between the output shaft 552 and the sample stage 140.

In the present embodiment, the shaker 112 is configured as an orbital shaker, i.e., the shaker 112 is configured to impart orbital motion to the sample stage 140 and consequently to the sample support 300 mounted to the sample stage 140. In this embodiment, the shaker 112 includes an eccentric drive coupling 156 and one or more eccentric guide couplings 160 mounted to the sample stage 140. The illustrated embodiment includes four eccentric guide couplings 160, although more or less than four may be provided. The positions of the eccentric drive coupling 156 and the eccentric guide couplings 160 may be distributed throughout the footprint of the sample stage 140 to distribute the shaking force imparted to the sample support 300. A shaft coupler 564 intercouples the motor 548 (via the output shaft 552) and the eccentric drive coupling 156. Hence, the motor 548 actively drives the orbital motion of the eccentric drive coupling 156 and in response the eccentric guide couplings 160 passively follow the actively driven orbital motion.

Figure 6:
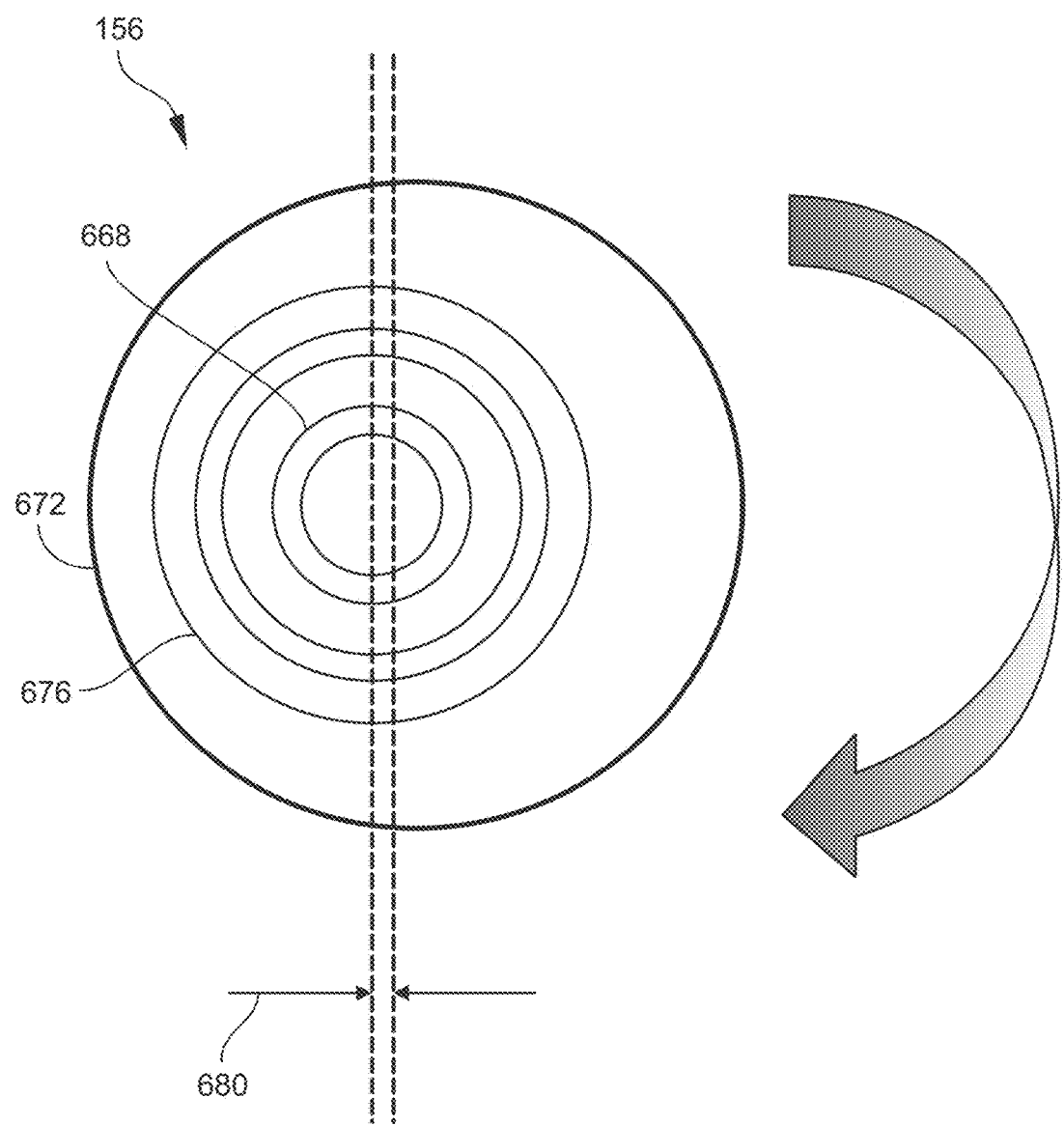
FIG. 6 is a plan view of an example of an eccentric drive coupling according to an embodiment.

FIG. 6 is a plan view of the eccentric drive coupling 156. The eccentric drive coupling 156 includes a drive shaft 668 attached to a drive eccentric 672 through a bearing 676 concentric with the drive shaft 668. The drive shaft 668 rotates coaxially with its central axis. In response to the rotation of the drive shaft 668, however, the drive eccentric 672, being eccentrically shaped, orbits about the central axis of the drive shaft 668, thereby imparting an orbital shaking motion to the sample stage 140 as appreciated by persons skilled in the art. The radial extent of the orbit relative to the central axis of the drive shaft 668 is defined by an offset 680, which for example may be one or a few millimeters.

Figure 7:
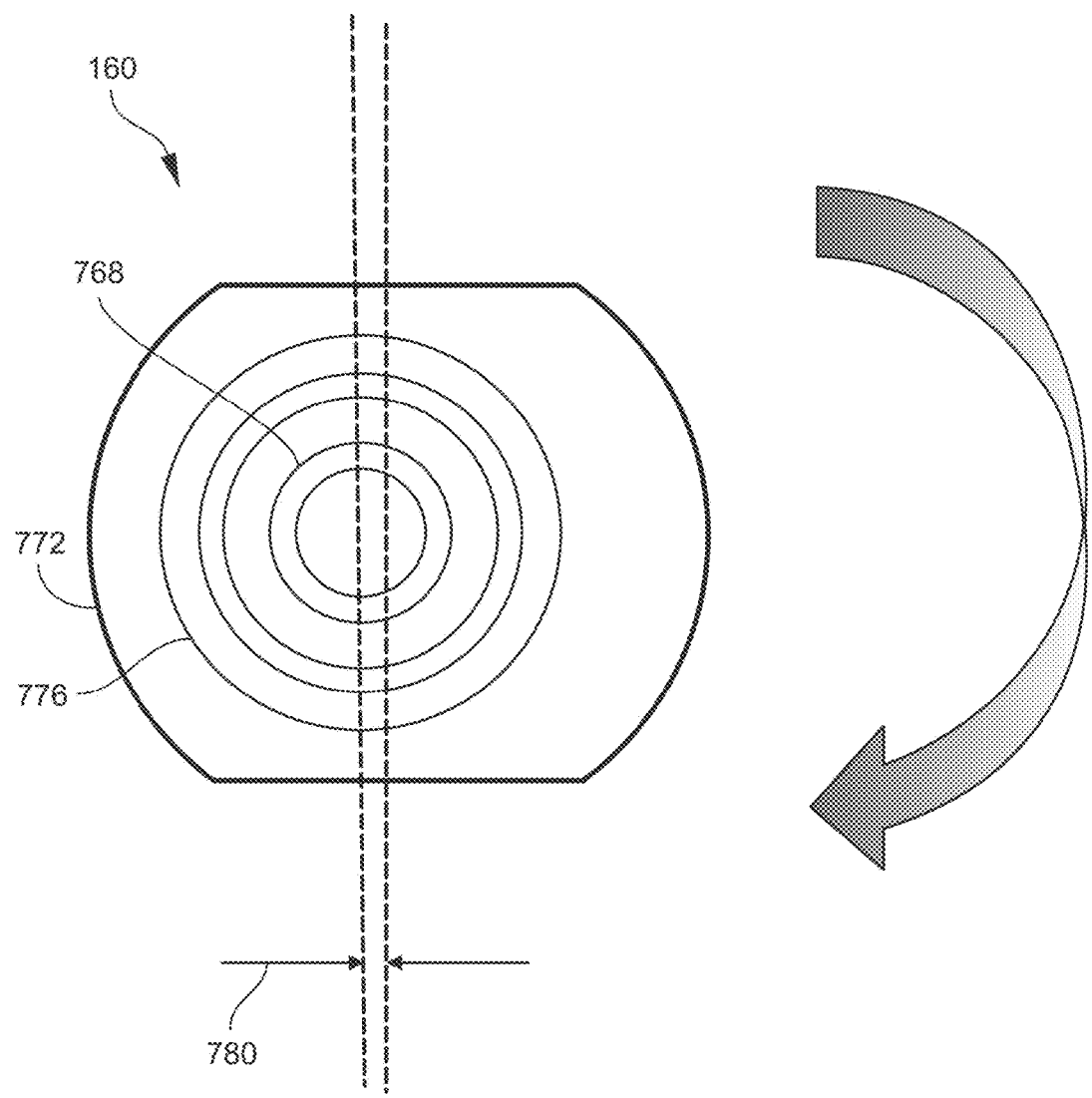
FIG. 7 is a plan view of an example of an eccentric guide coupling according to an embodiment.

FIG. 7 is a plan view of one of the eccentric guide couplings 160. The eccentric guide coupling 160 is structured and operates similarly to the eccentric drive coupling 156. Accordingly, the eccentric guide coupling 160 includes a guide shaft 768 attached to a guide eccentric 772 through a bearing 776 concentric with the guide shaft 768. The guide shaft 768 rotates coaxially with its central axis, while the guide eccentric 772 orbits about the central axis of the guide shaft 768, with an offset 780 having the same value as the offset 680 of the eccentric drive coupling 156. The guide shaft 768 is not actively driven, but rather rotates in response to the rotation of the drive shaft 668 directly driven by the motor 548 and the resulting orbital motion of the sample stage 140 and guide eccentric 772.

Referring to FIG. 4, the heater 104 may include one or more heater elements 184 positioned below the sample stage 140 and thus below the sample support 300 (FIG. 3) when mounted to the sample stage 140. In the present embodiment utilizing a multi-container sample support 300, the heater 104 includes a linear array of heater elements 184. Like the columns of the sample support 300, the heater elements 184 are linearly positioned and spaced from each other along the Y-axis (third axis or direction). The number of heater elements 184 is the same as the number of sample containers 336 provided in each column of the sample support 300 (eight in the present embodiment). The heater elements 184 have a heater-to-heater pitch, which is the same pitch as the well-to-well pitch P (FIG. 3) of the sample containers 336. Thus, when the heater elements 184 are positioned below any given column of sample containers 336, each heater element 184 may be associated with a corresponding one of the sample containers 336. Moreover, the centers of the heater elements 184 are able to be aligned with the respective centers of the sample containers 336 in the X-Y plane. The heater elements 184 may be cylindrical or have cylindrical portions. In an embodiment, the heater 104 is a resistive heating device, in which case the heater elements 184 may be composed of a material having good thermal conductivity, such as a metallic (metal or metal alloy) composition, and may be in thermal (typically physical) contact with a strip of electrically resistant material. In this case, the heater elements 184 may be heated by running an electrical current through the electrically resistant material, whereby the heat energy emitted from the electrically resistant material is transferred by heat conduction to the heater elements 184. Consequently, heat energy is emitted from the heater elements 184 and transferred to the sample containers 336 by convection.

Also in the present embodiment, the heater elements 184 are movable such that they can be indexed on a column-by-column basis. That is, the heater elements 184 are movable such that they can be sequentially aligned with each column of sample containers 336 of the sample support 300. For this purpose, the heater elements 184 are movable (translatable) in at least one horizontal (first) direction in the X-Y plane (along the X-axis in the present embodiment). In particular, the first direction is the direction along which columns are adjacent to each other, thereby allowing the heater elements 184 to address each column in succession. The heater elements 184 may also be movable (translatable) in the vertical (second) direction (along the Z-axis) to enable the heater elements 184 to be moved toward (raised) and away (lowered) from the sample containers 336 and thereby selectively apply heat energy to the sample containers 336.

As best illustrated in FIG. 2, the apparatus 100 includes a staging assembly 134. The staging assembly 134 includes a first stage 188 and a second stage 192 to effect movement of the heater elements 184. The first stage 188 is configured to move along the first (X) axis, and the second stage 192 is configured to move along the second (Z) axis. The first stage 188 is driven by a first stage motor 196 (e.g., a bi-directional stepper motor) coupled to the first stage 188 via a suitable transmission linkage 206, such as a toothed belt and pulley arrangement as illustrated. The movement of the first stage 188 may be guided by one or more first linear guides 110. The second stage 192 is driven by a second stage motor 214 (e.g., a bi-directional stepper motor) coupled to the second stage 192 via a suitable transmission linkage 218, such as a rack and pinion arrangement, screw drive, etc. The movement of the second stage 192 may be guided by one or more second linear guides 122. In the present embodiment, the second linear guides 122 are mounted to the first stage 188, and the second stage 192 is positioned between the first stage 188 and the sample stage 140. In addition, the heater elements 184 are mounted to the second stage 192. By this configuration, the second stage 192 (and thus the heater elements 184) moves toward and away from the sample stage 140 (and thus a sample support 300 mounted on the sample stage 140) relative to the first stage 188. Moreover, the first stage 188 moves the second stage 192 (and thus the heater elements 184) in the first (X) direction to sequentially address the columns of the sample support 300.

Referring to FIG. 4, the magnet assembly 108 may include one or more magnets 126 positioned below the sample stage 140 and thus below the sample support 300 (FIG. 3) when mounted to the sample stage 140. In the present embodiment utilizing a multi-container sample support 300, the magnet assembly 108 includes a linear array of magnets 126. Like the columns of the sample support 300 and the heater elements 184, the magnets 126 are linearly positioned and spaced from each other along the Y-axis (third axis or direction). The number of magnets 126 is the same as the number of sample containers 336 provided in each column of the sample support 300 (eight in the present embodiment). The magnets 126 have a magnet-to-magnet pitch, which is the same pitch as the well-to-well pitch P (FIG. 3) of the sample containers 336. Thus, when the magnets 126 are positioned below any given column of sample containers 336, each magnet 126 may be associated with a corresponding one of the sample containers 336. Moreover, the centers of the magnets 126 are able to be aligned with the respective centers of the sample containers 336 in the X-Y plane. The magnets 126 may be cylindrical (or ring-shaped). The magnets 126 may be permanent magnets (e.g., neodymium), or may be electromagnets.

Like the heater elements 184 in present embodiment, the magnets 126 are movable in at least the first (X) direction such that they can be sequentially aligned with each column of sample containers 336 of the sample support 300, and thereby address each column in succession. The magnets 126 may also be movable in the second (Z) direction to enable the magnets 126 to be moved toward and away from the sample containers 336 and thereby selectively apply the localized magnetic fields generated by the respective magnets 126 to the sample containers 336. The magnets 126 may thus be moved by X- and Z-stages. In the present embodiment, the magnets 126 are mounted to the same staging assembly 134 as the heater elements 184, and thus the staging assembly 134 may also be referred to as a heater/magnet staging assembly 134. The magnets 126 are mounted to the second stage 192, and thus the same first stage 188 and second stage 192 are utilized to move both the heater elements 184 and the magnets 126. This configuration reduces the number of motorized stages required, and allows the linear array of magnets 126 to be positioned adjacent to the linear array of heater elements 184. The heater elements 184 and the magnets 126 have a magnet-to-heater pitch, which is the pitch between each heater element 184 and corresponding magnet 126 adjacent to that heater element 184 along the first (X) direction. As evident from FIG. 4, the magnet-to-heater pitch may be the same as the well-to-well pitch P (FIG. 3) of the sample containers 336. Hence, the magnets 126 may be aligned with and apply magnetic fields to the respective sample containers 336 of one column, while the heater elements may be aligned with and 184 apply heat energy to the respective sample containers 336 of an adjacent column.

As best illustrated in FIG. 4, the sample stage 140 generally has two opposing end regions 438 adjoining two opposing side regions 442, and an opening 130 through the thickness of the sample stage 140 defined by inside edges of the end regions 438 and the side regions 442. The opening 130 is large enough to span the area of the entire array of sample containers 336 of the sample support 300 when mounted on the sample stage 140. The opening 130 thus exposes all sample containers 336 at the bottom side of the sample support 300, enabling the heater elements 184 and the magnets 126 to access all sample containers 336, i.e. enabling the heater elements 184 and the magnets 126 to be moved along the second (Z) direction into close proximity to the bottoms of the sample containers 336, and apply the heat energy and magnetic fields. Moreover, the eccentric drive coupling 156 is positioned at one of the end regions 438, and the eccentric guide couplings 160 are positioned at the side regions 442, which facilitates access to the bottoms of the sample containers 336 by the heater elements 184 and the magnets 126.

In an embodiment, the apparatus 100 may further include a home positioning device (not shown) configured to determine a home position of the second stage 192 and thus the heater elements 184 and the magnets 126. The home position may be a position at which the heater elements 184 or the magnets 126 are determined to be aligned with (or coaxial with, relative to the Z-axis) a given column of sample containers 336. If a misalignment is found, the first stage 188 may be adjusted to correct for the misalignment. For this purpose, the home positioning device may communicate with (provide feedback signals to) a system controller of the apparatus 100 that controls the operation of the staging assembly 134, as appreciated by persons skilled in the art. As non-limiting examples, the home positioning device may be a photo-interrupter, an optical encoder, a relay switch, or other appropriate sensor as appreciated by persons skilled in the art.

Figure 8:
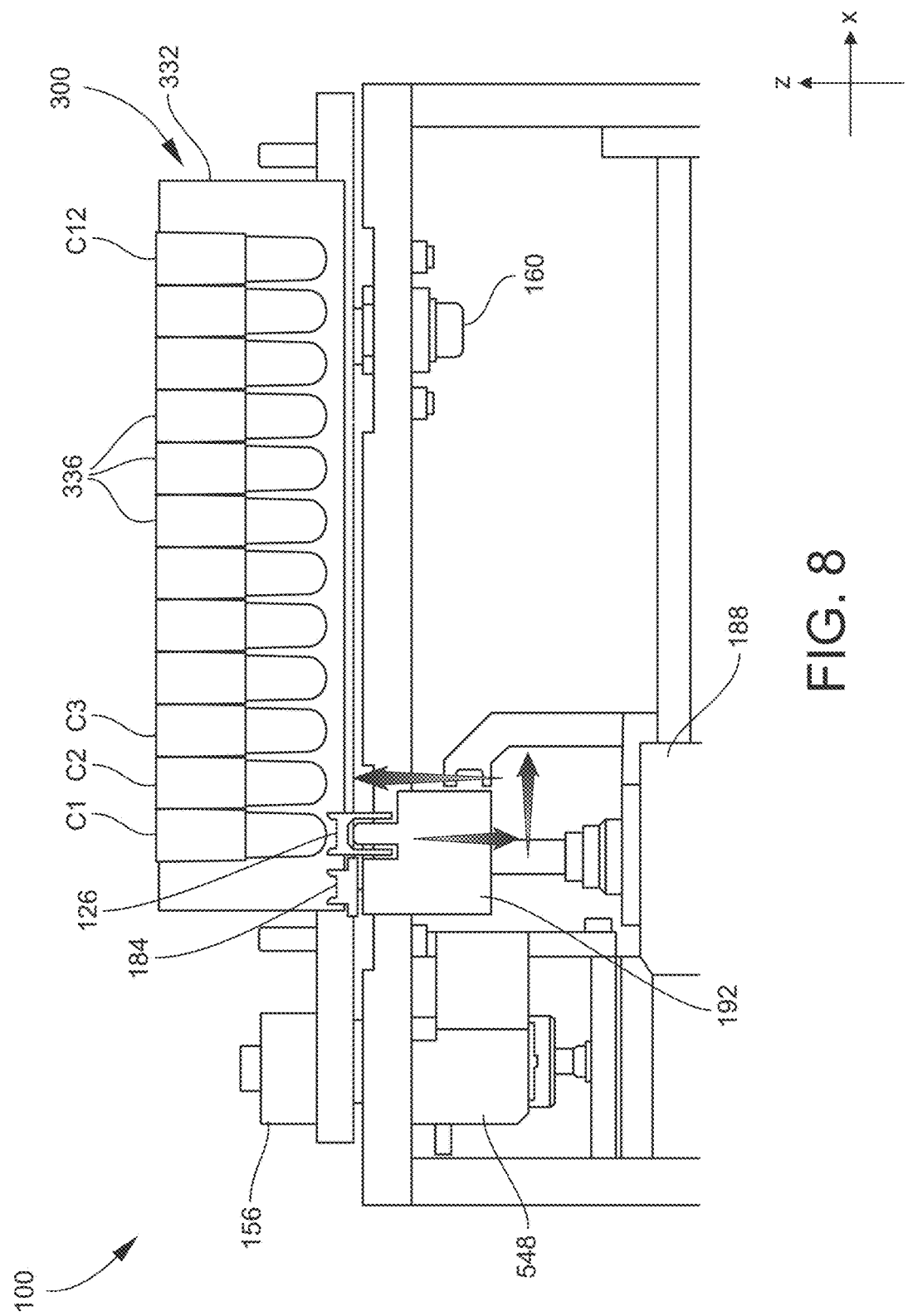
FIG. 8 is a side view of an upper portion of the sample processing apparatus illustrated in FIG. 1, illustrating a heater and magnet assembly in an upper first column position according to an embodiment.
Figure 9:
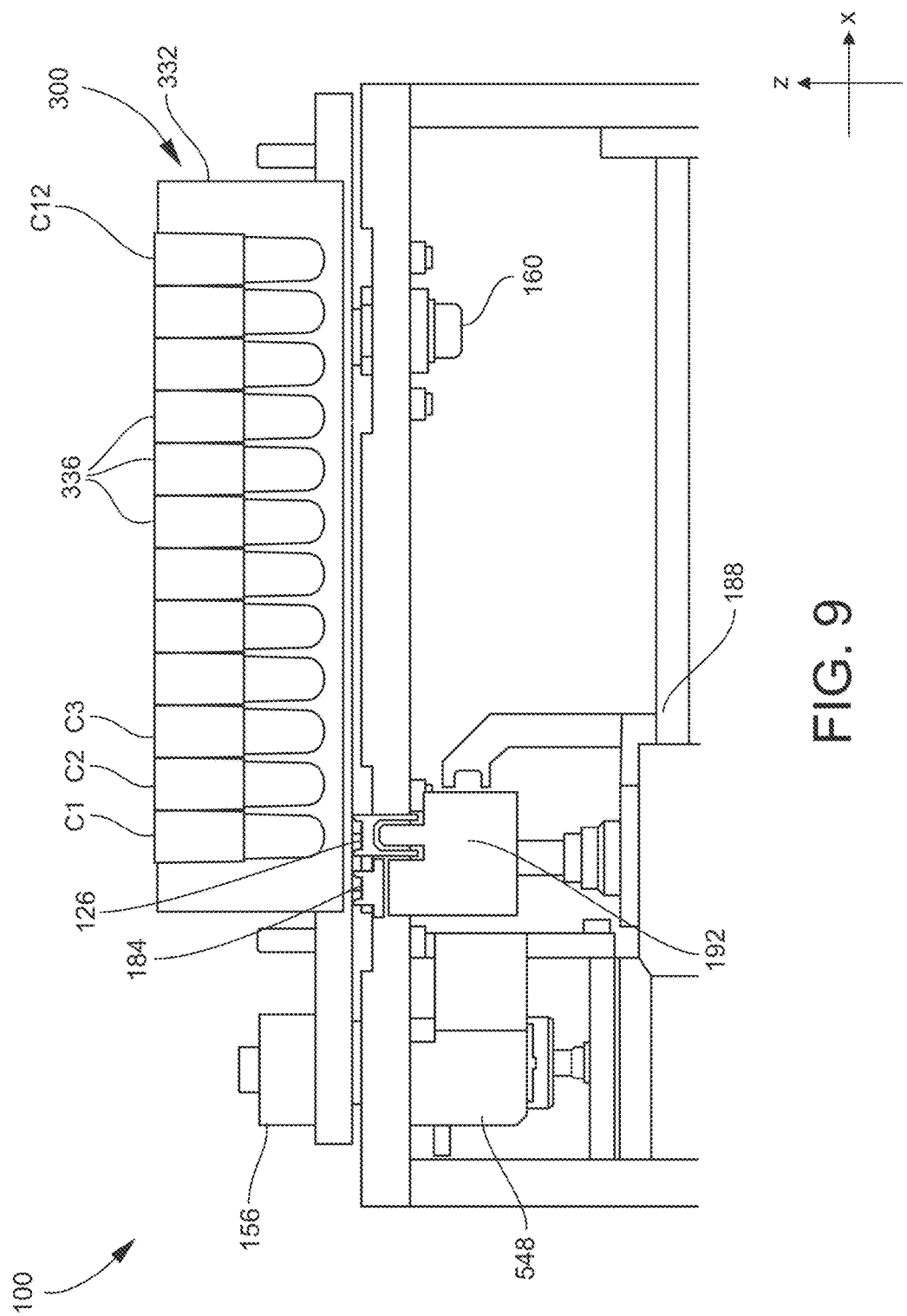
FIG. 9 is a side view of an upper portion of the sample processing apparatus illustrated in FIG. 1, illustrating the heater and magnet assembly in a lower first column position according to an embodiment.
Figure 10:
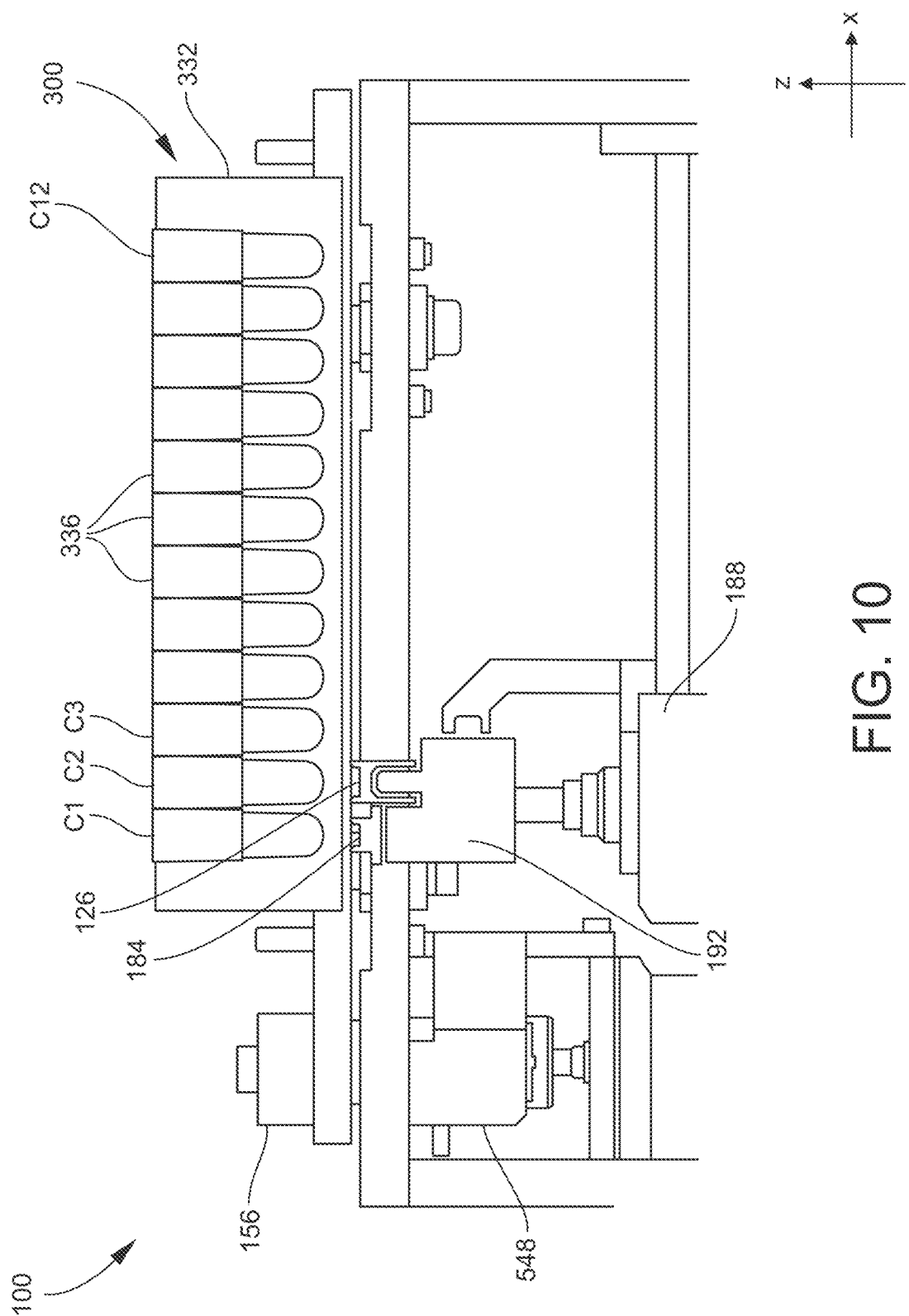
FIG. 10 is a side view of an upper portion of the sample processing apparatus illustrated in FIG. 1, illustrating the heater and magnet assembly in a lower second column position according to an embodiment.

FIGS. 8-11 illustrate the operation (particularly the movements) of the heater 104 and magnet assembly 108. Specifically, FIGS. 8-11 are side views of an upper portion of the apparatus 100, illustrating a sequence of movements of the heater 104 and magnet assembly 108 as implemented by the staging assembly 134. FIGS. 8-10 further illustrate a sample support 300 mounted on the sample stage 140. The sample support 300 is shown in cross-section so that the sample containers 336 are visible. The first three columns of sample containers 336 are labeled C1, C2, and C3, respectively, and the last column is labeled C12. In this example, the first column C1 has been arbitrarily selected to be the left-most column from the perspective of FIGS. 8-11. Accordingly, the progression of movement of the heater 104 and magnet assembly 108 in the first (X) direction (or column-to-column direction) is from the left to the right from the perspective of FIGS. 8-11.

FIG. 8 shows the heater 104 and magnet assembly 108 in an initial or first column position relative to the columns. The magnet assembly 108 precedes the heater 104 in the first (X) direction, which may also be referred to as the column-to-column direction. Hence, in the first column position the magnets 126 are aligned (vertically, in the second (Z) direction) with the first column C1, while the heater elements 184 are located outside of the footprint of the array of sample containers 336 (under the left end of the sample support 300) and thus are not in alignment with any of the columns. In the first column position, the heater 104 may be OFF (or inactive), such that the heater elements 184 are not actively emitting heat energy. At the first column position and all subsequent column positions, the heater 104 and magnet assembly 108 may be movable between an upper (or raised) position and a lower (or lowered) position relative to the second (Z) direction.

FIG. 8 shows the upper first column position, at which the magnets 126 are in close proximity to the sample containers 336 of the first column C1. In the upper first column position, the samples contained in the sample containers 336 of the first column C1 are immersed in the respective magnetic fields generated by the magnets 126, or at least are immersed in the strong regions of the magnetic fields. Stated differently, in the upper first column position, the magnets 126 are spaced at a close distance from the bottoms of the sample containers 336 at which the magnetic fields applied to the sample containers 336 are effective for their intended purpose (such as, for example, pulling magnetic beads down to the bottoms of the sample containers 336. By comparison, FIG. 9 shows the lower first column position, at which the heater elements 184 and the magnets 126 are more remotely spaced from the sample containers 336. In the lower first column position, the sample containers 336 are no longer immersed in the magnetic fields, or at least are no longer immersed in the strong regions of the magnetic fields. Stated differently, in the lower first column position, the magnets 126 are spaced at a remote distance from the bottoms of the sample containers 336 at which the magnetic fields applied to the sample containers 336 are not effective for their intended purpose. At any of the lower column positions, the heater 104 may be OFF or at least may be at a great enough distance away from the sample containers 336 that an insignificant amount of heat energy will be deposited into the sample containers 336. Likewise, at any of the upper column positions, the heater 104 may be OFF if not being utilized to heat the column of sample containers 336 above the heater elements 184.

The heater 104 and magnet assembly 108 may be held in the upper first column position shown in FIG. 8 for any desired period of time, depending on the type of sample processing being implemented. The heater 104 and magnet assembly 108 may then be indexed to a second column position in the following manner. First, the heater 104 and magnet assembly 108 are lowered, as depicted by a downward arrow in FIG. 8, from the upper first column position shown in FIG. 8 to the lower first column position shown in FIG. 9. The heater 104 and magnet assembly 108 are lowered by translating the second stage 192 downward as described above. In the lower first column position, the magnets 126 are still aligned with the first column C1 and the heater elements 184 are still located outside of the footprint of the array of sample containers 336, but the heater elements 184 and the magnets 126 are now positioned remotely from the sample containers 336.

Next, with the heater 104 and magnet assembly 108 still in the lower first column position, the heater 104 and magnet assembly 108 are translated one step forward, as depicted by a rightward arrow in FIG. 8, from the lower first column position to the lower second column position shown in FIG. 10. At the lower second column position, the magnets 126 are aligned with (but remotely spaced from) the second column C2 and the heater elements 184 are aligned with (but remotely spaced from) the first column C1. The heater 104 and magnet assembly 108 are translated one step forward by translating the first stage 188 forward as described above.

Figure 11:
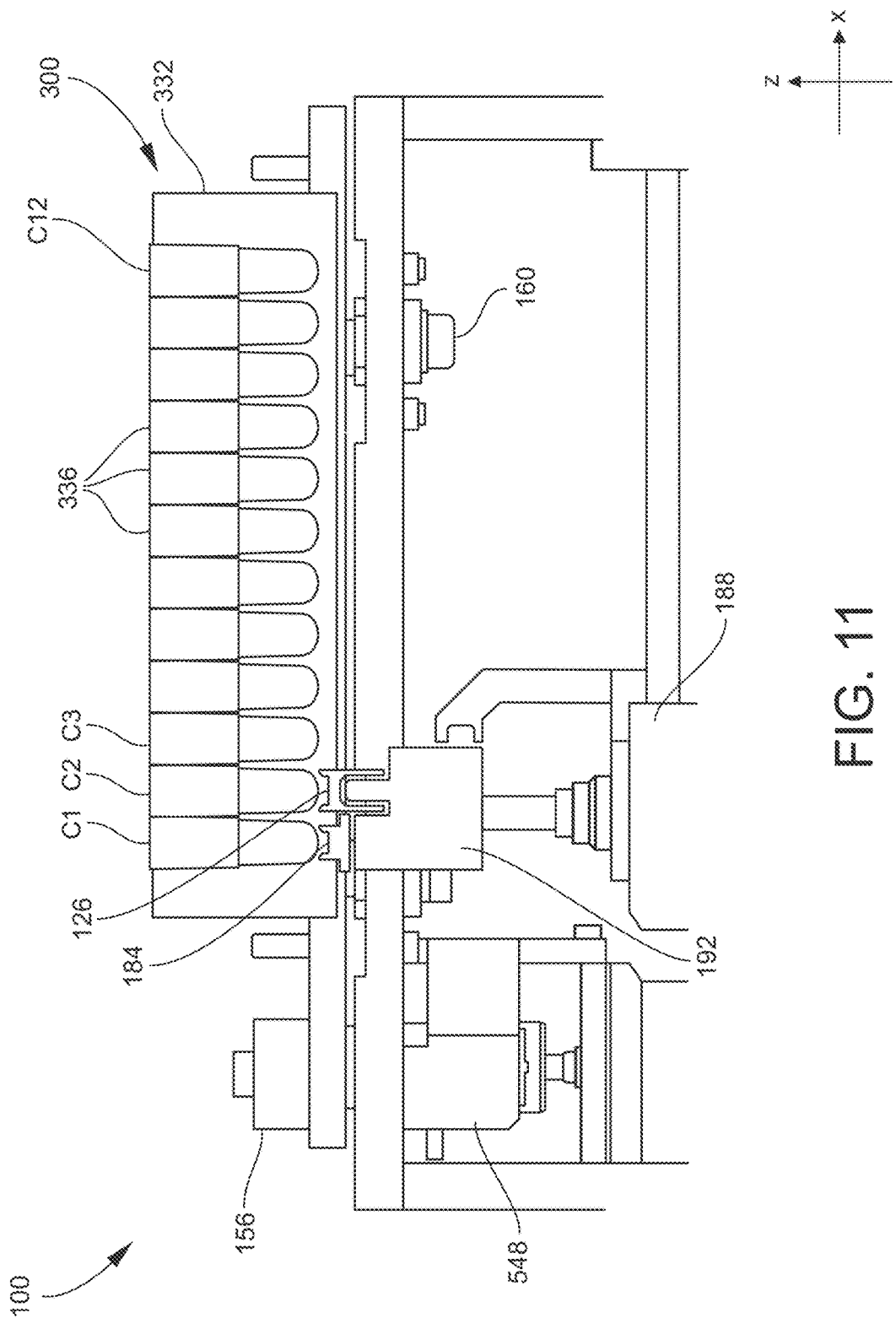
FIG. 11 is a side view of an upper portion of the sample processing apparatus illustrated in FIG. 1, illustrating the heater and magnet assembly in an upper second column position according to an embodiment.

Next, with the heater 104 and magnet assembly 108 still at the lower second column position, the heater 104 and magnet assembly 108 are raised (see upward arrow in FIG. 8) from the lower second column position to the upper second column position shown in FIG. 11. The heater 104 and magnet assembly 108 are raised by translating the second stage 192 upward as described above. In the upper second column position, if the heater 104 is ON, the samples contained in the sample containers 336 of the first column C1 are exposed to the heat energy emitted from the heater elements 184. Also in the upper second column position, the samples contained in the sample containers 336 of the second column C2 are immersed in the respective magnetic fields generated by the magnets 126, or at least in the strong regions of the magnetic fields. By this configuration, the magnetic fields and the heat energy may be sequentially applied the first column C1, and subsequently to each successive column of the array of sample containers 336.

The heater 104 and magnet assembly 108 may be held in the upper second column position shown in FIG. 11 for any desired period of time, depending on the type of sample processing being implemented. The heater 104 and magnet assembly 108 may then be indexed to the next (third) column position, at which the magnets 126 are aligned with the third column C3 and the heater elements 184 are aligned with the second column C2. This sequence of movement, shown in FIGS. 8-11 and further depicted by the arrows in FIG. 8, may be repeated until all columns of sample containers 336 of the sample support 300 have been processed, i.e., subjected to the magnetic fields and the heat energy. In some embodiments, the last column position may correspond to the heater elements 184 being aligned with the last (twelfth in the present example) column C12, and the magnets 126 being located outside of the footprint of the array of sample containers 336 (under the right end of the sample support 300) and not in alignment with any of the columns.

Hence, the apparatus 100 enables a magnetic field to be applied to a plurality of samples (such as in the same column of sample containers 336) simultaneously, and subsequently heat energy to be applied to the same set of samples simultaneously. Additionally, the shaker 112 may be operated at any time as called for by the method being performed. If needed, the heater 104 and magnet assembly 108 may be lowered to the lower position to provide clearance for the shaker 112 to operate. Thus, the apparatus 100 enables a wide variety of sample processing protocols to be implemented utilizing a combination of heating, shaking, and magnetic field application. The apparatus 100 integrates all three operations of heating, shaking, and magnetic field application at a single station, i.e., at the apparatus 100. Thus, conventional separate stations respectively dedicated for heating, shaking, and magnetic field application are not required. This integrated configuration reduces the overall footprint of the hardware required to carry out heating, shaking, and magnetic field application. The integrated configuration also eliminates the need to transport samples from one station to another, thereby increasing processing throughput (reducing processing time) and reducing the risk of contaminating the samples.

Generally, the magnet assembly 108 may be utilized for any protocol entailing the application of a magnetic field to a sample. As one non-limiting example, the magnet assembly 108 may be utilized for magnetic beads separation. In magnetic beads separation, magnetic beads are added to the sample to form a suspension in which the magnetic beads are distributed throughout the liquid phase of the sample. The size of the beads may be on the order of nanometers (e.g., up to about 1000 nm, or 1 micrometer (μm)), or on the order of micrometers (e.g., from about 1 μm to about 1000 μm). The beads may be composed of silica or other suitable material, as appreciated by persons skilled in the art. The beads are rendered magnetic (responsive to a magnetic field) by being coated with iron oxide or other suitable magnetic material. The magnetic material may be a permanent magnetic material, or may be a material that is permanently or temporarily magnetized by the magnetic field. For convenience in the present disclosure, the term "magnetic" encompasses all such materials. The beads may also be functionalized with probes or ligands having a composition that specifically binds to the analytes of the sample (or target compounds of interest) desired to be separated and isolated from the sample. The analytes may be biological compounds such as nucleic acids, which may be hybridized nucleic acids. Alternatively, the analytes may be chemical compounds. After the magnetic beads have been added to a sample, such as in one of the sample containers 336 of the sample support 300, analytes in the sample will bind to (be captured by) the magnetic beads (or to probes or ligands of the magnetic beads, depending on the embodiment). The magnet assembly 108 is then moved to the upper position at which one of the magnets 126 is proximate to the bottom of the corresponding sample container 336, thereby immersing the sample in the magnetic field generated by the magnet 126, as described herein. In response, the analyte-bearing magnetic beads are attracted to the magnet 126 and hence are pulled down to the bottom of the sample container 336, whereby the captured analytes are concentrated at the bottom of the sample container 336. Subsequently, the liquid phase of the sample may be removed by aspiration (e.g., pipetting) and/or evaporation. The magnetic particles may then be washed in a suitable solvent to release the analytes from the magnetic particles. The solvent containing the analytes may then be aspirated from the sample container 336. The analytes may then be further processed or analyzed as required by the particular protocol being implemented.

Generally, the heater 104 may be utilized for any protocol entailing heating a sample, such as for temperature regulation or temperature programming, or for evaporating a volatile liquid phase of the sample. As one non-limiting example, a protocol (e.g., in conjunction with magnetic-based separation) may involve adding a volatile solvent such as an alcohol (e.g., ethanol, isopropanol, etc.) to the sample container 336. The heater 104 may be utilized to evaporate the solvent in the sample container 336, such as after the magnetic beads have been pulled down to the bottom of the sample container 336.

Generally, the shaker 112 may be utilized for any protocol entailing shaking or agitation of a sample. As examples, the shaking of the sample(s) in one or more sample containers 336 may be implemented for mixing, homogenization, enhancement of chemical reaction or other interaction between two or more components of the sample, distribution or resuspension of magnetic beads in the sample, etc.

As an example, a method for processing samples will now be described. The method may be performed using the apparatus 100 including the heater 104, the magnet assembly 108, and the shaker 112 as described herein. A sample support is provided. The sample support includes a plurality of sample containers arranged as an array of a plurality of columns and a plurality of rows. The plurality of columns includes at least a first column and a second column adjacent to the first column. The first column contains one or more samples in one or more respective sample containers of the first column, and the second column contains one or more samples in one or more respective sample containers of the second column. The sample support is mounted to a sample stage such that the sample support covers an opening of the sample stage. The opening has an area (size) allowing the sample containers to be exposed through the opening. A plurality of magnets are moved into proximity with bottoms of the sample containers of the first column. Magnetic fields generated by the magnets are applied to the sample containers of the first column to expose the one or more samples of the first column to one or more of the magnetic fields. The plurality of magnets are moved into proximity with bottoms of the sample containers of the second column, while the sample support remains mounted to the sample stage. A plurality of heater elements are moved into proximity with the bottoms of the sample containers of the first column. Heat energy emitting from the heater elements is applied to the sample containers of the first column to expose the one or more samples of the first column to the heat energy.

The plurality of columns include one or more additional columns. The heater elements and the magnets may be sequentially moved on a column-by-column basis, and the steps of applying magnetic fields and applying heat energy may be repeated one or more times, until the magnetic fields and the heat energy have been successively applied to the sample containers of the first column, the second column, and at least one of the additional columns.

The method may also include shaking the samples with the use of the apparatus 100 described herein. For example, the samples may be shaken between one or more iterations of applying magnetic fields and applying heat energy to the samples.

As another example, a method for processing samples containing nucleic acids such as DNA will now be described. The method may be performed using the apparatus 100 including the heater 104, the magnet assembly 108, and the shaker 112 as described herein. The steps are as follows:

1) Liquid buffer carrying DNA is dispensed into one or more columns of an array of sample containers provided by a sample support, such as wells of a microplate.

2) Magnetic beads are added to the sample containers, and the shaker is started to obtain homogeneous mixing and allow binding of the DNA to the magnetic beads.

3) The shaker is turned off, and the magnets are moved to one column of the sample containers containing the DNA, whereby the magnetic beads are pulled down by the magnetic fields to the bottoms of the sample containers.

4) After all of the magnetic beads have settled down to the container bottoms, the buffer is aspirated from the sample containers and discarded.

5) Ethanol is then added to the sample containers as a wash step.

6) The shaker is restarted to disperse the ethanol and the magnetic beads in the sample containers.

7) The shaker is turned off, and the magnetic beads are pulled down by the magnets. In preparation for the shaking of step 6, the magnets may have been moved away from the sample containers to provide clearance for the shaking action, in which case the magnets are moved back to sample containers after the shaker is turned off in step 7.

8) After all of the magnetic beads have settled back down to the container bottoms, the ethanol is aspirated from the sample containers.

9) Steps 5-8 are repeated for one or more cycles, for example two cycles.

10) The heater elements are then moved to the column and activated to evaporate the ethanol, and the magnetic beads are allowed to air-dry.

11) A suitable solvent is dispensed into the sample containers, and consequently the DNA elutes from the magnetic beads.

12) The magnets (appropriately repositioned if necessary) are then utilized to cause the magnetic beads to settle down to the container bottoms.

13) The solvent, now carrying the DNA, is aspirated from the sample containers, enabling the DNA to be further processed or analyzed, such as by an instrument separate from the apparatus 100.

The foregoing steps may be repeated for one or more other columns of the sample container array.

Referring to FIGS. 1 and 2, the apparatus 100 may also include a system controller (e.g., a computer or computing device) 146. The system controller 146 may schematically represent one or more modules (or units, or components) configured for controlling, monitoring and/or timing various functional aspects of the apparatus 100 such as, for example, the operations of the heater 104, the magnet assembly 108, the shaker 112, the first stage 188 (e.g., a motor coupled to the first stage 188, or a motor controller communicating with the motor), second stage 192 (e.g., a motor coupled to the second stage 192, or a motor controller communicating with the motor), a home positioning device, etc. One or more modules may be, or be embodied in, for example, a computer workstation or desktop computer, or a mobile computing device such as a laptop computer, portable computer, tablet computer, handheld computer, personal digital assistant (PDA), smartphone, etc. The system controller 146 may also be configured for providing and controlling a user interface that provides screen displays of objects or data with which a user may interact, such as maps of sample supports 300, fields for inputting data and control parameters of the apparatus 100, etc. The system controller 146 may include one or more reading devices on or in which a non-transitory (tangible) computer-readable (machine-readable) medium may be loaded that includes instructions for performing all or part of any of the methods disclosed herein. For all such purposes, the system controller 146 may be in signal communication with various components of the apparatus 100 via wired or wireless communication links. Also for these purposes, the system controller 146 may include one or more types of hardware, firmware, other types of electronics, and/or software, as well as one or more memories, databases, user input devices, and user output devices. Examples of user input devices include, but are not limited to, a keyboard, keypad, touch screen, mouse, joystick, trackball, light pen, other pointing devices, microphone, etc. Examples of user output devices include, but are not limited to, a display screen, printer, visual indicators such as lamps or light-emitting diodes LEDs), audible indicators such as loudspeakers, etc.

It will be understood that one or more of the processes, sub-processes, and process steps described herein may be performed by hardware, firmware, other types of electronics, software, or a combination of two or more of the foregoing, on one or more electronic or digitally-controlled devices. The software may reside in a software memory (not shown) in a suitable electronic processing component or system such as, for example, the system controller 146 schematically depicted in FIG. 1. The software memory may include an ordered listing of non-transitory executable instructions for implementing logical functions (that is, "logic" that may be implemented in digital form such as digital circuitry or source code, or in analog form such as an analog source such as an analog electrical, sound, or video signal). The instructions may be executed within a processing module, which includes, for example, one or more microprocessors, general purpose processors, combinations of processors, digital signal processors (DSPs), application specific integrated circuits (ASICs), field-programmable gate array (FPGAs), etc. Further, the schematic diagrams describe a logical division of functions having physical (hardware and/or software) implementations that are not limited by architecture or the physical layout of the functions. The examples of systems described herein may be implemented in a variety of configurations and operate as hardware/software components in a single hardware/software unit, or in separate hardware/software units.

The executable instructions may be implemented as a computer program product having instructions stored therein which, when executed by a processing module of an electronic system (e.g., the system controller 146 in FIG. 1), direct the electronic system to carry out the instructions. The computer program product may be selectively embodied in any non-transitory computer-readable storage medium for use by or in connection with an instruction execution system, apparatus, or device, such as an electronic computer-based system, processor-containing system, or other system that may selectively fetch the instructions from the instruction execution system, apparatus, or device and execute the instructions. In the context of this disclosure, a computer-readable storage medium is any non-transitory means that may store the program for use by or in connection with the instruction execution system, apparatus, or device. The non-transitory computer-readable storage medium may selectively be, for example, an electronic, magnetic, optical, electromagnetic, infrared, or semiconductor system, apparatus, or device. A non-exhaustive list of more specific examples of non-transitory computer readable media include: an electrical connection having one or more wires (electronic); a portable computer diskette (magnetic); a random access memory (electronic); a read-only memory (electronic); an erasable programmable read only memory such as, for example, flash memory (electronic); a compact disc memory such as, for example, CD-ROM, CD-R, CD-RW (optical); and digital versatile disc memory, i.e., DVD (optical). Note that the non-transitory computer-readable storage medium may even be paper or another suitable medium upon which the program is printed, as the program may be electronically captured via, for instance, optical scanning of the paper or other medium, then compiled, interpreted, or otherwise processed in a suitable manner if necessary, and then stored in a computer memory or machine memory.

It will also be understood that the term "in signal communication" or "in electrical communication" as used herein means that two or more systems, devices, components, modules, or sub-modules are capable of communicating with each other via signals that travel over some type of signal path. The signals may be communication, power, data, or energy signals, which may communicate information, power, or energy from a first system, device, component, module, or sub-module to a second system, device, component, module, or sub-module along a signal path between the first and second system, device, component, module, or sub-module. The signal paths may include physical, electrical, magnetic, electromagnetic, electrochemical, optical, wired, or wireless connections. The signal paths may also include additional systems, devices, components, modules, or sub-modules between the first and second system, device, component, module, or sub-module.

More generally, terms such as "communicate" and "in . . . communication with" (for example, a first component "communicates with" or "is in communication with" a second component) are used herein to indicate a structural, functional, mechanical, electrical, signal, optical, magnetic, electromagnetic, ionic or fluidic relationship between two or more components or elements. As such, the fact that one component is said to communicate with a second component is not intended to exclude the possibility that additional components may be present between, and/or operatively associated or engaged with, the first and second components.

It will be understood that various aspects or details of the invention may be changed without departing from the scope of the invention. Furthermore, the foregoing description is for the purpose of illustration only, and not for the purpose of limitation—the invention being defined by the claims.

What is claimed is:

1. A sample processing apparatus, comprising:
   a sample stage having an opening and configured to support a sample support such that the sample support covers the opening;
   a first stage configured to move along a first axis;
   a second stage configured to move alternately toward and away from the opening along a second axis orthogonal to the first axis, the second stage coupled to the first stage wherein the second stage is movable with the first stage along the first axis;
   a plurality of heater elements disposed on the second stage and linearly positioned along a third axis orthogonal to the first axis and the second axis; and
   a plurality of magnets disposed on the second stage and linearly positioned along the third axis, wherein:
   the magnets are positioned adjacent to the heater elements such that each magnet is spaced from a respective one of the heater elements along the first axis;
   the first stage is configured to sequentially move the heater elements and the magnets to a plurality of column positions along the first axis, wherein at each column position, at least the heater elements or the magnets are aligned with a column of sample containers of the sample support when the sample support is mounted to the sample stage, the column being arranged along the third axis; and
   the second stage is configured to, at each column position, move the heater elements and the magnets between an upper position at which the heater elements and the magnets are proximate to the sample support when the sample support is mounted to the sample stage, and a lower position at which the heater elements and the magnets are remote from the sample support.

2. The sample processing apparatus of claim 1, wherein:
the heater elements are spaced from each other by a heater-to-heater pitch;
the magnets are spaced from each other by a magnet-to-magnet pitch equal to the heater-to-heater pitch;
each magnet is spaced from a respective one of the heater elements along the first axis by a magnet-to-heater pitch equal to the heater-to-heater pitch; and
at each column position, the first stage is configured to align at least the heater elements or the magnets with respective sample containers of the sample support when the sample support is mounted to the sample stage.

3. The sample processing apparatus of claim 1, wherein the plurality of column positions comprises at least one column position at which the heater elements are aligned with a first column of sample containers of the sample support when the sample support is mounted to the sample stage, and the magnets are simultaneously aligned with a second column of sample containers adjacent to the first column.

4. The sample processing apparatus of claim 1, wherein the sample stage is configured to shake the sample support when the sample support is mounted to the sample stage.

5. The sample processing apparatus of claim 4, wherein the sample stage comprises an end region and a side region at partially defining the opening, and further comprising a drive coupling coupled to the end region and a guide coupling coupled to the side region, wherein the drive coupling is configured to induce movement of the guide coupling and shake the sample stage.

6. The sample processing apparatus of claim 4, wherein the sample stage is configured to shake the sample support in an orbital motion.

7. The sample processing apparatus of claim 1, wherein at the upper position the heater elements and the magnets are in or extend through the opening.

8. A method for processing samples, the method comprising:
providing a sample support comprising a plurality of sample containers arranged as an array of a plurality of columns and a plurality of rows, wherein the plurality of columns comprises at least a first column and a second column adjacent to the first column, the first column contains one or more samples in one or more respective sample containers of the first column, and the second column contains one or more samples in one or more respective sample containers of the second column;
mounting the sample support to a sample stage such that the sample support covers an opening of the sample stage, wherein the opening has an area allowing the sample containers to be exposed through the opening;
moving a plurality of magnets into proximity with bottoms of the sample containers of the first column;
applying magnetic fields generated by the magnets to the sample containers of the first column to expose the one or more samples of the first column to one or more of the magnetic fields;
moving the plurality of magnets into proximity with bottoms of the sample containers of the second column, while the sample support remains mounted to the sample stage;
moving a plurality of heater elements into proximity with the bottoms of the sample containers of the first column; and
applying heat energy emitting from the heater elements to the sample containers of the first column to expose the one or more samples of the first column to the heat energy.

9. The method of claim 8, comprising applying the magnetic fields to the sample containers of the second column.

10. The method of claim 9, comprising moving the heater elements into proximity with the bottoms of the sample containers of the second column, and applying heat energy to the sample containers of the second column.

11. The method of claim 8, wherein the plurality of columns comprises one or more additional columns, and further comprising sequentially moving the heater elements and the magnets to one or more of the additional columns, and repeating the steps of applying magnetic fields and applying heat energy one or more times, until the magnetic fields and the heat energy have been successively applied to the sample containers of the first column, the second column, and at least one of the additional columns.

12. The method of claim 8, wherein at least one of the samples comprises a liquid and a plurality of magnetic beads added to the liquid, and applying the magnetic field to the sample container containing the at least one sample pulls the magnetic beads to a bottom of the sample container.

13. The method of claim 12, wherein the at least one sample comprises a plurality of target compounds that bind to the magnetic beads after the magnetic beads are added to the liquid, and applying the magnetic field to the sample container containing the at least one sample concentrates the target compounds at the bottom of the sample container.

14. The method of claim 8, wherein at least one of the samples comprises a liquid, and applying the heat energy to the sample container containing the at least one sample evaporates the liquid.

15. The method of claim 8, comprising shaking the sample stage to agitate the samples.

16. The method of claim 15, comprising shaking the sample stage during a time period selected from the group consisting of:
before applying the magnetic fields to the sample containers of the first column;
after applying the magnetic fields to the sample containers of the first column, and before applying heat energy to the sample containers of the first column; and
both of the foregoing.

17. The method of claim 8, wherein the number of sample containers provided in each column is equal to a number selected from the group consisting of: the number of magnets; the number of heater elements; and both of the foregoing.

18. The method of claim 8, wherein moving the plurality of magnets into proximity with bottoms of the sample containers of the second column, and moving the plurality of heater elements into proximity with the bottoms of the sample containers of the first column, are performed simultaneously.

19. The method of claim 8, wherein:
the columns are adjacent to each other along a first axis;
the heater elements and the magnets are mounted to a heater/magnet stage;
moving a plurality of magnets into proximity with the bottoms of the sample containers of the first column, and moving the plurality of magnets into proximity with the bottoms of the sample containers of the second column, are performed by moving the heater/magnet stage along the first axis from a first column position to a second column position.

20. The method of claim 8, wherein:

the columns are adjacent to each other along a first axis;

the heater elements and the magnets are mounted to a staging system comprising a first stage configured to move along a first axis and a second stage configured to move along a second axis orthogonal to the first axis, wherein the second stage is coupled to the first stage such that the second stage is movable with the first stage along the first axis, and the heater elements and the magnets are positioned on the second stage;

moving the plurality of magnets into proximity with the bottoms of the sample containers of the first column comprises moving the second stage along the second axis toward the sample support;

moving the plurality of magnets into proximity with the bottoms of the sample containers of the second column, and moving the plurality of heater elements into proximity with the bottoms of the sample containers of the first column, comprise:
- moving the second stage along the second axis away from the sample support;
- moving the first stage along the first axis from a first column position to a second column position;
- while at the second column position, moving the second stage along the second axis toward the sample support.

* * * * *